United States Patent

Katner

[11] 4,301,282
[45] Nov. 17, 1981

[54] 1-OXA-β-LACTAM ANTIBIOTICS

[75] Inventor: Allen S. Katner, Indianapolis, Ind.

[73] Assignee: Eli Lilly and Company, Indianapolis, Ind.

[21] Appl. No.: 187,862

[22] Filed: Sep. 17, 1980

[51] Int. Cl.³ .......................................... C07D 413/14
[52] U.S. Cl. .................................................... 544/90
[58] Field of Search ........................................ 544/90

[56] References Cited

U.S. PATENT DOCUMENTS 4,013,653  3/1977  Wolfe ............................. 260/244 R
4,138,486  2/1979  Narisada ............................. 544/90
4,226,866  10/1980 Christensen et al. ........... 424/248.51

OTHER PUBLICATIONS

Williams, "Detoxication Mechanisms" 2nd Ed. pp. 396–402, John Wiley & Sons, Inc, New York, (1959).

Primary Examiner—John M. Ford
Attorney, Agent, or Firm—William B. Scanlon; Arthur R. Whale

[57] ABSTRACT

Bicyclic 1-oxa-β-lactam diacid antibiotics represented by the formula

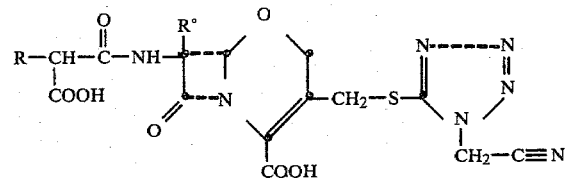

wherein R is phenyl, hydroxyphenyl, acetoxyphenyl, alkylphenyl, or halophenyl, thienyl or furyl; R° is H or OCH₃; and the pharmaceutically acceptable non-toxic salts thereof are broad spectrum antibiotics useful for controlling infections in man and animals. The compounds are prepared by reacting the corresponding 3-halomethyl diester with 1-cyanomethyl-1H-tetrazole-5-thiol followed by deesterification.

10 Claims, No Drawings

1-OXA-β-LACTAM ANTIBIOTICS

SUMMARY

Bicyclic 1-oxa-β-lactam antibiotics represented by the formula

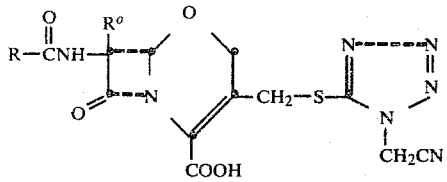

wherein R is α-carboxybenzyl, α-carboxy-substituted benzyl, eg. α-carboxy-p-hydroxybenzyl, α-carboxythienylmethyl, or α-carboxyfurylmethyl; $R_1$ is hydrogen or methoxy; and the pharmaceutically acceptable salts thereof, are broad spectrum antibiotics useful in combatting microorganisms pathogenic to man and animals. The antibiotics are prepared by displacement of the halogen of the corresponding 7-(α-carboxy)acylamino-3-halomethyl-1-oxa-β-lactam compound with 1-cyanomethyl-1H-tetrazole-5-thiol.

BACKGROUND OF THE INVENTION

Bicyclic β-lactam antibiotics of the type represented by the above formula which have a four-membered β-lactam ring fused to a six-membered oxazine ring have been described by Narisada et al., U.S. Pat. No. 4,138,486 and Belgium Pat. No. 863,998. For example, Narisada et al., described the 1-oxa-β-lactam compound substituted in the 3-position of the oxazine ring with the 1-methyl-1H-tetrazol-5-ylthiomethyl group and in the 7-position with a phenylmalonamido group as represented by the following formula.

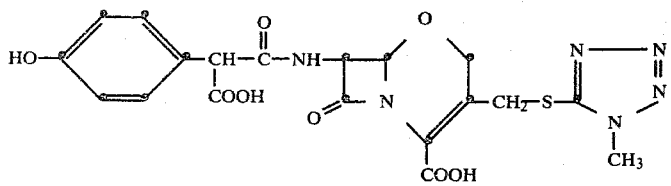

Because of the high antibacterial activity of this new type of β-lactam antibiotic research workers have been stimulated to search for even more potent antibiotics of this bicyclic type.

The compounds of this invention, although related to the compounds described by Narisada et al., differ structurally by having a cyanomethyl substituted tetrazole moiety at the 3-position of the six-membered oxazine ring.

DETAILED DESCRIPTION

The antibiotic compounds of this invention are represented by the following structural formula 1.

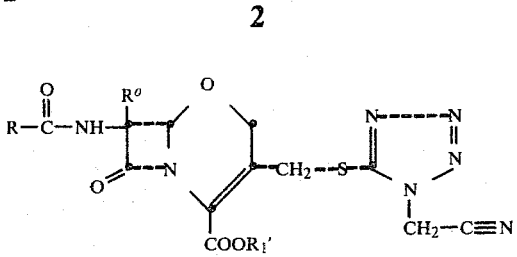

wherein R is an α-carboxy substituted arylmethyl group of the formulae

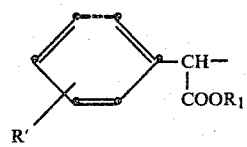

wherein
R' is hydrogen, hydroxy, protected hydroxy, acetoxy, $C_1$–$C_3$ alkyl, or halogen,

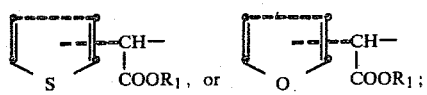

$R^o$ is hydrogen or methoxy;
$R_1$ and $R_1'$ are hydrogen, or a carboxy protecting group; when $R_1$ and $R_1'$ are hydrogen, the pharmaceutically acceptable non-toxic salts thereof.

In the above formula "$C_1$–$C_3$ alkyl" refers to methyl, ethyl, n-propyl and iso-propyl; and halogen refers to bromo, chloro, or fluoro.

The term, "carboxylic acid protecting group" refers to ester groups commonly employed to protect the carboxy group in β-lactam antibiotics and includes the haloalkyl groups such as 2,2,2-trichloroethyl, 2,2,2-tribromoethyl, and 2-iodoethyl; the arylalkyl groups and substituted arylalkyl groups such as benzyl, halobenzyl, p-methoxybenzyl, p-nitrobenzyl, diphenylmethyl, 4,4'-dimethoxydiphenylmethyl, the phenacyl group and the substituted phenacyl groups such as chlorophenacyl, bromophenacyl, methylphenacyl, and nitrophenacyl, and the trialkylsilyl groups such as trimethylsilyl. Preferred carboxy protecting groups of this invention are the diphenylmethyl (benzhydryl) and p-methoxybenzyl ester groups.

The term "protected hydroxy", refers to the phenolic hydroxy temporarily protected with a common phenolic protecting group such as a lower alkanoyl group for example acetyl, propionyl and the like; α-haloalkanoyl such as chloroacetyl, trifluoroacetyl, trichloroacetyl, and the like; alkoxycarbonyl and arylalkoxycarbonyl protecting groups such as t-butyloxycarbonyl, 2,2,2-trichloroethoxycarbonyl, benzyloxycarbonyl, p-nitrobenzyloxycarbonyl, diphenylmethoxycarbonyl, and the like; and arylalkyl groups such as benzyl, diphenylmethyl and trityl. A preferred hydroxy protecting group is the tetrahydropyranyl group. Another preferred group is the trityl protecting group.

The function of the carboxy and hydroxy protecting groups is to block these otherwise reactive groups during the syntheses of the compounds of the formula 1 to prevent untoward reactions.

The compounds of the invention as shown in the formula 1 are dicarboxylic acids ($R_1$ and $R_1' = H$) which are capable of forming salts with suitable inorganic and organic bases. Such salts include the pharmaceutically acceptable, non-toxic salts such as the sodium, potassium, calcium, ammonium, cyclohexylammonium, dicylohexylammonium, dibenzylammonium, monoethanolammonium, di-ethanolammonium, and procaine salts. These salts are prepared with the diacid by following the procedures commonly used to form salts of carboxylic acids. For example, a solution of the diacid in an organic solvent can be extracted with an aqueous solution of a base such as sodium hydroxide or sodium carbonate and the extract evaporated to dryness or lyophilized to the salt as a powder. The ammonium salt can be prepared by adding ammonium hydroxide to a solution of the diacid in an aqueous organic solvent. Amine salts are prepared by adding two equivalents of the amine, or a slight excess, to a solution of the diacid in a substantially anhydrous organic solvent.

The compounds of the formula 1 are formally named by the ACS nomenclature system as 5-oxa-1-azabicyclo[4.2.0]oct-2-ene-2-carboxylic acids. For example, the compound represented by the formula when R is α-carboxybenzyl, $R^o$ is methoxy, and $R_1$ is hydrogen is formally named as 7β-[[carboxy(phenyl)acetyl]acetyl]amino]-7-methoxy-8-oxo-3-[[[1-cyanomethyl-1H-tetrazo-5-yl]thio]methyl]-5-oxa-1-azabicyclo[4.2.0]oct-2-ene-2-carboxylic acid. For convenience herein the compounds of the formula 1 are referred to arbitrarily as 1-oxa-β-lactams which has reference to the nucleus of the following formula.

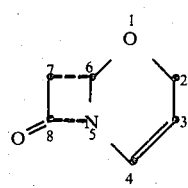

The compounds of the formula 1 are prepared by reacting a 7-acylamino-3-halomethyl-1-oxa-β-lactam as a diester with 1-cyanomethyl-1H-tetrazole-5-thiol as depicted in the following reaction scheme

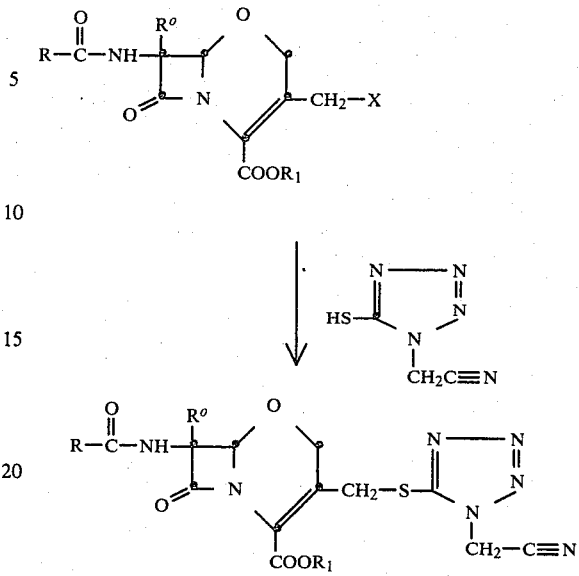

wherein R and R° have the same meanings as in formula 1, $R_1$ is an ester group as defined in formula 1, and X is chloro, bromo or iodo.

The reaction is carried out in an inert solvent at a temperature between about 15° C. and about 55° C. although somewhat higher temperatures up to about 70° C. can be tolerated. An excess of the tetrazole thiol in the salt form, e.g., the sodium salt, is added to a solution of the 3-halomethyl-1-oxa-β-lactam compound in an aqueous organic solvent containing an acid binding agent. Preferably the reaction is carried out in a two-phase reaction mixture comprising an inert, water-immiscible organic solvent such as a halogenated hydrocarbon solvent, for example methylene chloride or di- or trichloroethane, and an aqueous solution of 1-cyanomethyl-1H-tetrazole-5-thiol sodium salt containing excess sodium hydroxide. A quaternary ammonium halide such as a tetralkylammonium halide, e.g. tetra-n-butylammonium chloride, is added to the reaction mixture to facilitate the reaction. The reaction carried out in the two-phase system is conveniently carried out at or near room temperatures.

The 7-acylamino-3-halomethyl-1-oxa-β-lactam starting material is prepared as described in Belgium Pat. No. 863,998. For example, one of the 7-acylamino-3-chloromethyl-1-oxa-β-lactams described is the 7-(p-toluamido)-3-chloromethyl ester compound. This compound can be N-deacylated by the two-step N-descylation procedure described by U.S. Pat. No. 3,697,515, by forming an imino halide with phosphorus pentachloride in an inert solvent and by then treating the imino halide with an alcohol such as methyl alcohol or iso-butyl alcohol to form the corresponding imino ether. Hydrolysis of the imino ether under mild conditions provides the 7-amino-3-chloromethyl-1-oxa ester.

Alternatively, the 7-acylamino-3-halomethyl-1-oxa ester can be N-deacylated by the method described by U.S. Pat. No. 4,211,702.

The 7-amino-3-chloromethyl-1-oxa ester is then acylated at the 7-amino group with the desired phenylmalonic acid, thienyl or furylmalonic acid wherein one of the carboxylic acid groups is protected with a readily removable carboxy-protecting group. The remaining free carboxylic acid group is then converted to an active derivative for the N-acylation. Active derivatives which can be used are for example, the mixed anhydrides formed with methyl or iso-butyl chloroformate, or the active ester formed with hydroxybenzotriazole (HBT).

Alternatively, the compounds of the formula 1 can be prepared by reacting a 3-chloromethyl-7-acylamino-1-oxa-β-lactam ester described by Belgium Pat. No. 863,998 with 1-cyanomethyl-1H-tetrazole-5-thiol to provide the corresponding 3-(1-cyanomethyl-1H-tetrazol-5-ylthiomethyl)substituted compound. The latter can be N-deacylated by the methods described above to provide the 7-amino-3-(1-cyanomethyl-1H-tetrazol-5-ylthiomethyl)-1-oxa-β-lactam ester. The latter is then acylated with the arylmalonic acid half ester as described above to provide a compound of the formula 1.

Alternatively, the compounds represented by the formula 1 can be obtained by the methods and procedures described by Narisada, et al., U.S. Pat. No. 4,138,486. The substitutuion of 1-cyanomethyl-1H-tetrazole-5-thiol for the heterocyclic thiols employed therein provides the compounds of the formula 1.

Among the compounds of this invention represented by the formula 1 are the following:

| R | R° | $R_1$ |
|---|---|---|
| α-carboxybenzyl | OCH3 | H |
| α-carboxy-4-hydroxybenzyl | OCH3 | H |
| α-carboxy-4-hydroxybenzyl | OCH3 | Na |
| α-carboxy-4-hydroxybenzyl | H | H |
| α-(p-methoxybenzyloxy-carbonyl)-4-hydroxybenzyl | OCH3 | DPM[1] |
| α-carboxy-4-chlorobenzyl | OCH3 | H |
| α-carboxy-4-chlorobenzyl | H | H |
| α-carboxy-3-chlorobenzyl | OCH3 | H |
| α-carboxy-3-hydroxybenzyl | OCH3 | H |
| α-carboxy-3-hydroxybenzyl | H | H |
| α-carboxy-4-acetoxybenzyl | OCH3 | H |
| α-carboxy-4-methylbenzyl | H | H |
| α-carboxy-4-methylbenzyl | OCH3 | Na |
| α-carboxy-3-acetoxybenzyl | OCH3 | K |
| α-carboxy-2-thienylmethyl | OCH3 | H |
| α-carboxy-2-thienylmethyl | H | H |
| α-carboxy-3-thienylmethyl | H | H |
| α-carboxy-3-thienylmethyl | OCH3 | H |
| α-carboxy-2-furylmethyl | OCH3 | H |

[1]DPM = diphenylmethyl

Preferred compounds of the invention are represented by the following structural formula

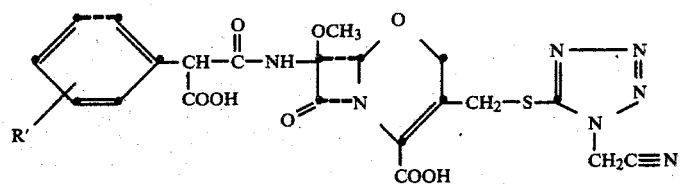

wherein R' is hydrogen, hydroxy or acetoxy. An especially preferred compound of this invention is represented by the following structural formula.

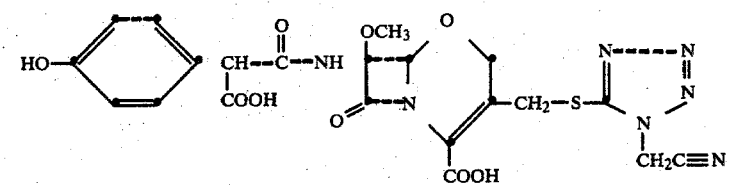

The hydroxy and carboxy protected intermediate useful in the preparation of the above preferred compound and represented by the following formula is also a preferred compound of this invention:

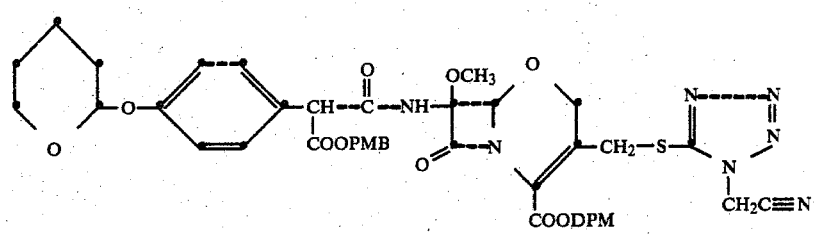

wherein pMB represents p-methoxybenzyl and DPM represents diphenylmethyl. The foregoing preferred compound (free acid) is formally named as 7β-[[carboxy(4-hydroxyphenyl)acetyl]amino]-7α-methoxy-8-oxo-3-[[[1-cyanomethyl-1H-tetrazol-5-yl]thio]methyl]-5-oxa-1-azabicyclo]4.2.0]oct-2-ene-2-carboxylic acid.

The preparation of the above preferred compound wherein R' is p-hydroxy is carried out by employing an esterified and hydroxy protected derivative of the 3-halomethyl-1-oxa-β-lactam represented by the formula.

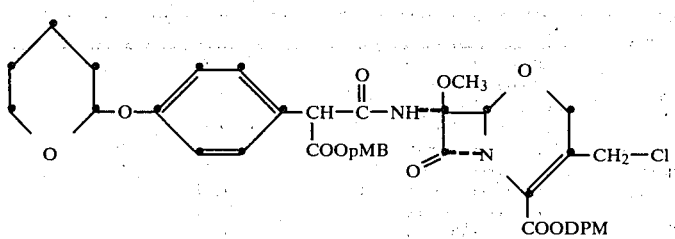

The above-protected 3-halomethyl compound is first reacted with a basic aqueous solution of 1-cyanomethyl-1H-tetrazole-5-thiol in methylene chloride as described hereinabove. The two-phase reaction mixture contains the quaternary salt, tetra-n-butylammonium chloride. The intermediate, 3-(1-cyanomethyl-1H-tetrazol-5-yl)thiomethyl substituted derivative, is reacted at 0° C. with hydrochloric acid in acetone to remove the tetrahydropyran hydroxy-protecting group to provide the esterified intermediate of the formula.

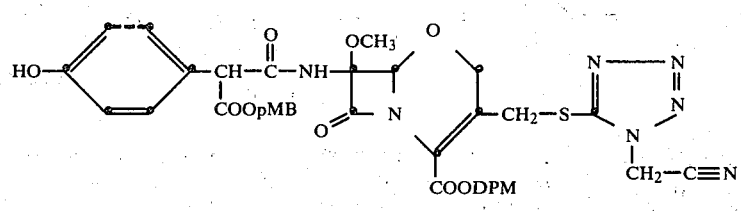

The above diester is deesterified at about 10° C. by reacting the diester in anisole with an excess of aluminum chloride. The product, the diacid compound, is best purified by reverse phase silica gel HPLC using 12% acetonitrile, 2% acetic acid, 86% water.

The stereochemical configuration of the 1-oxa-β-lactam antibiotics of this invention is the same as that of the compounds described by Narisada, et al. The 7-position side chain has the β-configuration, the 7-methoxy substituent, (R°=OCH$_3$), has the α-configuration, while the ring juncture of bicyclic rings is as depicted below.

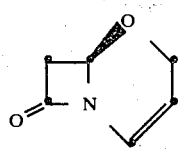

The assymetric carbon atom in the 7-position side chain preferrably has the D-configuration although mixtures of the D- and L-configurations possess a high order of antibacterial activity.

The compounds of this invention (formula 1, $R_1=R_1'=H$) inhibit the growth of microorganisms pathogenic to man and animals. They are useful in the free acid form or in the salt form for the control and treatment of infections caused by gram-positive and gram-negative microorganisms when administered parenterally. The compounds can be formulated in suitable dosage unit form for injection or they can be added to various iv. fluids such as saline or dextrose for administration by the iv. drip method.

The following Table I lists the minimum inhibitory concentrations against a number of microorganisms exhibited by a preferred 1-oxa-β-lactam compound of the invention as determined by the agar dilution method.

TABLE I

Antibacterial Activity
7β-[dl-[carboxy(4-hydroxyphenyl)acetyl]amino]-7α-methoxy-8-oxo-3-[[[1-cyanomethyl-1H-tetrazol-5-yl]thio]methyl]-5-oxa-1-azabicyclo[4.2.0]oct-2-ene-2-carboxylic acid

| Organism | Strain | Minimum Inhibitory Concentration (mcg/ml) |
|---|---|---|
| Staphlococcus aureus | X1.1 | 8 |
| Staphlococcus aureus | V41 | 16 |
| Staphlococcus aureus | X400 | 64 |
| Staphlococcus aureus | S13E | 32 |
| Staphlococcus epidermidis | EPI1 | 64 |
| Staphlococcus epidermidis | EPI2 | 128 |
| Streptococcus Group A | C203 | 2 |
| Streptococcus group D | X66 | >128 |
| Streptococcus group D | 9960 | >128 |
| Haemophilus influenzae | BRUN[1] | 32 |
| Haemophilus influenzae | 251[2] | 64 |
| Shigella sonnei | N9 | .125 |
| Escherichia coli | N10 | 1 |
| Escherichia coli | EC14 | .125 |
| Escherichia coli | TEM | .125 |
| Klebsiella sp. | X26 | .25 |
| Klebsiella sp. | KAE | 16 |
| Enterobacter aerogenes | X68 | .25 |
| Enterobacter aerogenes | C32 | .25 |
| Enterobacter aerogenes | EB17 | 125 |
| Enterobacter cloacae | EB5 | .5 |
| Enterobacter cloacae | 265A | 16 |
| Salmonella sp. | X514 | 8 |
| Salmonella sp. | 1335 | 8 |
| Pseudomonas aeruginosa | X528 | 16 |
| Pseudomonas aeruginosa | X239 | 16 |
| Pseudomonas aeruginosa | Ps18 | 32 |
| Serratia marcescens | X99 | .25 |
| Serratia marcescens | X99 | .25 |
| Serratia marcescens | SE3 | 8 |
| Proteus morganii | PR15 | 8 |
| Proteus inconstans | Pr33 | .125 |
| Proteus rettgeri | C24 | .125 |
| Proteus rettgeri | PR7 | 16 |
| Citrobacter freundii | CF17 | 16 |
| Bordetella bronchoseptica | 16 | 32 |

[1]Sensitive strain.
[2]Resistant strain

The 1-cyanomethyl-1H-tetrazole-5-thiol used in the above preparation is prepared as follows. Ethyl azidoacetate is heated at a temperature of about 125° C. with an excess of cyanogen chloride to form 5-chloro-1H-tetrazole-1-ylacetate as a crystalline solid. The latter product is converted to the 5-thiol by heating the 5-chloro tetrazole with sodium hydrosulfide in an organic solvent such as ethyl alcohol. The reaction is carried out satisfactorily at the reflux temperature in ethyl alcohol for about 20–24 hours. The thiol is recovered by concentrating the reaction mixture and extracting with an organic solvent, for example, ethyl acetate.

The ethyl 5-thiol-1H-tetrazole-1-ylacetate product is then converted to the amide by heating the 5-thiol ester in a mixture of concentrated ammonium hydroxide, ammonium chloride and ethyl alcohol. The amide is recovered as the ammonium salt. The amide, 5-thiol-1H-tetrazol-1-ylacetamide ammonium salt, is then dehydrated to 1-cyanomethyl-1H-tetrazol-5-thiol. The dehydration of the amide is carried out by heating a solution of the amide in an inert organic solvent with a dehydrating agent in the presence of a hydrogen halide acceptor.

The dehydration of the amide in the last step of the reaction scheme can be carried out in an inert organic solvent such as a halogenated hydrocarbon solvent for example, methylene chloride, chloroform, a di- or trichloroethane, such as 1,2-dichloroethane and 1,1,2-trichloroethane.

Dehydrating agents which can be used in preparing the 1-cyanomethyl tetrazole include phosphorus oxychloride, phosphorus pentachloride, phosphorus pentoxide or thionyl chloride. Phosphorus oxychloride is the preferred dehydrating agent.

The preparation of the cyanomethyl tetrazole 5-thiol is illustrated in the following reaction scheme.

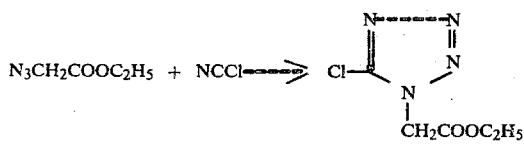

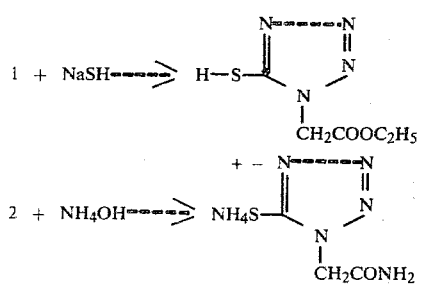

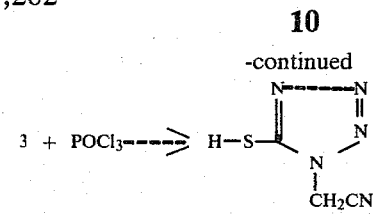

The following Examples further illustrate the invention.

EXAMPLE 1

7β-[dl-[Carboxy(4-hydroxyphenyl)acetyl]amino]-7α-methoxy-8-oxo-3-[[[1-cyanomethyl-1H-tetrazol-5-yl]thio]methyl]-5-oxa-1-azabicyclo[4.2.]oct-2-ene-2-carboxylic acid To a solution of 1.62 g (2 mmole) of 7β-[dl-[4-methoxybenzyloxycarbonyl(4-tetrahydropyran-2-yloxyphenyl)acetyl]amino]-7α-methoxy-8-oxo-3-(chloromethyl)-5-oxa-1-azabicyclo[4.2.0]oct-2-ene-2-carboxylic acid diphenylmethyl ester in 12 ml of methylene chloride containing 200 mg of tetra-n-butylammonium chloride was added a solution of 366 mg (2.6 mmole) of 1-cyanomethyl-1H-tetrazol-5-thiol in 4 ml of 0.5 N sodium hydroxide and 4 ml of water. The two phase reaction mixture was stirred at room temperature for 2 hr after which the organic phase was separated and dried over anhydrous sodium sulfate. The dried organic phase was then chromatographed over a two inch thick silica gel pad in a Buchner funnel using first 400 ml of 25% ethyl acetate in methylene chloride (by volume) for elution. The product was eluted with the 25% ethyl acetate eluant which was evaporated to dryness. There were obtained 1.15 g of the product represented by the following formula.

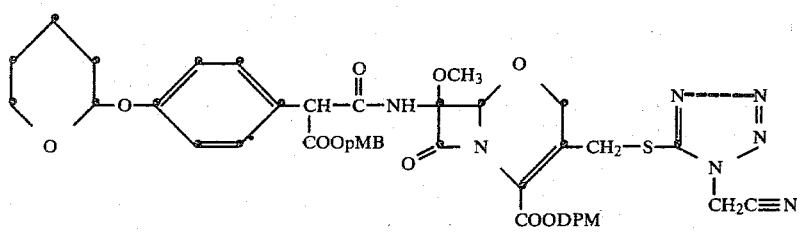

The tetrahydropyran protecting group was removed from the above product as follows.

To a solution of 1.1 g (1.2 mmole) of the above product in 12 ml of acetone cooled in an ice bath to a temperature of about 0° C. was added 0.2 ml of concentrated hydrochloric acid. The solution was stirred in the cold for 15 min. and then evaporated to dryness. The residue was dissolved in methylene chloride and the solution was washed with water and brine and was dried over sodium sulfate. The dried solution was evaporated to dryness. The product represented by the following formula was obtained as a reddish foam weighing 0.95 g.

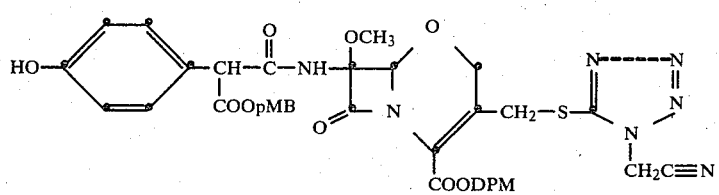

The above product was de-esterified as follows. A solution of 0.95 g (1.14 mmole) of the above product was dissolved in 10 ml of anisole under nitrogen with the aid of sonication and the solution was cooled to −10° C. in an ice-ethyl alcohol bath. A solution of 600 mg of aluminum chloride (4.5 mmole) in 3 ml of anisole was slowly added dropwise over 10 min. to the cold solution. The reaction mixture was stirred for one hour at −10° C. and for one hour while warming to room temperature. A solution containing 8 ml of ethyl acetate, 4 ml of water and 0.13 ml of concentrated hydrochloric acid was added with stirring to the chilled reaction mixture. An insoluble clump of product formed and acetone was added to form a solution. The organic layer was separated and evaporated to dryness under reduced pressure. The product, obtained as a crude gum, was dissolved in ethyl acetate and the solution washed with water and brine. Fresh water was added to the solution and the pH adjusted to 7.4 with 5 N sodium hydroxide. The aqueous layer containing the disodium salt of the de-esterified product was washed twice with 50 ml portions of ethyl acetate. Fresh ethyl acetate was added to the aqueous basic solution and the pH adjusted to 2.3 with 20% hydrochloric acid with vigorous stirring. The ethyl acetate layer was separated, washed with brine, dried over sodium sulfate and evaporated to dryness. There were obtained 370 mg of the title compound as a golden foam.

The product was purified as follows.

The impure de-esterified product, 370 mg, was chromatographed over reverse phase silica gel HPLC using 10% acetonitrile:2% acetic acid:88% water (by volume) as eluent. The chromatogram was monitored by UV. Fractions 31–40 were combined and evaporated to remove the acetonitrile. The aqueous residue was lyophilized and yielded 8.2 mg of the title compound represented by the following formula.

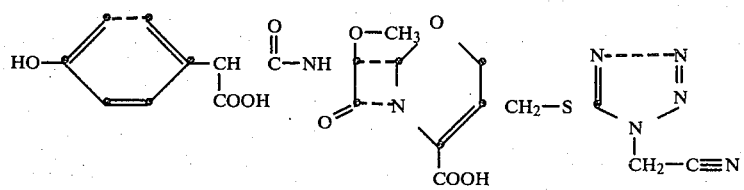

NMR (90 MHz, DMSO-$d_6$) delta: 3, 36 (s, 7-methoxy), 4.24 (s, c-3′-methylene), 4.44 (m, methine proton of side chain), 4.62 (s, C-2 methylene), 4.96 (s, C-6 H), 5.72 (s, methylene of cyanomethyl), 6.84 (m, phenyl), and 9.08–9.24 (two s, 7-NH and phenolic OH) ppm.

Preparation of 1-cyanomethyl-1H-tetrazol-5-thiol

A. Ethyl azidoacetate

To a solution of 490 g. (4 moles) of ethyl chloroacetate in 1500 ml. of acetonitrile were added 260 g. (4 moles) of sodium azide, and the mixture was heated at the reflux temperature for 20 hours. After heating, the reaction mixture was poured into 1 liter of water with stirring for ½ hour. The organic phase was separated from the aqueous phase and evaporated in vacuo to dryness. The yellow residual oil was dissolved in 1200 ml. of diethyl ether and the solution was dried over magnesium sulfate. Evaporation of the diethyl ether in vacuo gave 391 g. (76% yield) of ethyl azidoacetate.

B. Ethyl 5-chloro-1H-tetrazol-1-ylacetate

A mixture of 130 g. (1 mole) of ethyl azidoacetate prepared as described in Part A and 96 g. (1.56 mole) of cyanogen chloride was heated at a temperature of 125° C. for 20 hours. After the reaction mixture had cooled, the reaction product mixture was dissolved in ethyl acetate, and the solution was filtered and evaporated in vacuo yielding a yellow crystalline mass of product. The yellow crystals were recrystallized from aqueous ethyl alcohol and gave 149 g. (78% yield) of ethyl 5-chloro-1H-tetrazol-1-ylacetate as pale yellow crystals melting at about 57°–60° C.

C. Ethyl 5-thiol-1H-tetrazol-1-ylacetate

A solution of 209 g. of the chlorotetrazole ester, prepared as describd in part B above, and 250 g. of sodium hydrosulfide in 5 liters of ethyl alcohol was heated at the reflux temperature for 24 hours. After heating, the reaction mixture was acidified with concentrated hydrochloric acid, and the volume of the acidified mixture was reduced to ¼ the original volume by evaporation in vacuo,. The concentrate was extracted with ethyl acetate, the extract was dried and evaporated to dryness under reduced pressure. The residual product was recrystallized from toluenemethylene chloride-hexane and gave 129 g. of the product melting at about 85° C. to 88° C.

D. 5-Thiol-1H-tetrazol-1-ylacetamide ammonium salt

A solution of 20 g. (0.106 mole) of the tetrazolthiol ester, prepared as described above in part C, in 320 ml. of concentrated ammonium hydroxide and 200 ml. of ethyl alcohol containing 500 ml. of ammonium chloride was heated at the reflux temperature for about 12 hours. After heating, the reaction mixture was evaporated in vacuo, and the yellow crystalline residue obtained was recrystallized from hot ethyl alcohol to yield a first crop of 13.7 g. (73% yield) of the product as white crystals melting at about 197° to about 199° C. after vacuum drying. A second crop of 1.4 g. of the product was obtained which melted at about 191°-193° C.

E. 1-Cyanomethyl-1H-tetrazol-5-thiol

A suspension of 5.28 g. of the tetrazolamide ammonium salt, prepared as described above in part D, in 90 ml. of methylene chloride containing 14.4 ml. of pyridine was cooled to a temperature of about 0° C. To the suspension was added dropwise with stirring a solution of 4.6 g. (30 mmole) of phosphorous oxychloride in 40 ml. of methylene chloride. After the addition was completed, the reaction mixture was heated at the reflux temperature for 30 minutes and was then cooled to room temperature with stirring. The reaction mixture had turned orange after heating and contained some precipitate. The reaction mixture was evaporated to dryness in vacuo and the residue dissolved in ethyl acetate-water, 1:1, v:v. The pH of the solution was adjusted to pH 2 with 20% aqueous hydrochloric acid. The acidified solution was then extracted twice with 75 ml. portions of ethyl acetate and the extracts combined. The extract was then washed with 5% hydrochloric acid, with brine, was dried over sodium sulfate and evaporated in vacuo. The brown oil obtained as a residue crystallized on standing. The crystals were vacuum dried at room temperature and yielded after drying 2.6 g. (61% yield) of light brown product melting at about 113°-114° C.

The above reaction was repeated on a 10.6 g. batch of the tetrazol amide ammonium salt and 3.7 g. of the nitrile as off-white crystals melting at about 116°-118° C. were obtained.

The following analytical data were obtained for the crystalline product.

Elemental analysis calcualted for $C_3H_3N_5S$: Theory: C, 25.53; H, 2.14; N, 49.62. Found: C, 25.82; H, 2.40; N, 49.91.

The mass spectrum of the crystalline product showed a molecular weight of 141 in agreement with the product.

I claim:
1. A compound of the formula

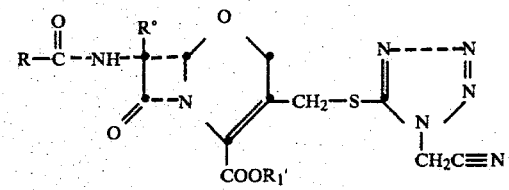

wherein R is an α-carboxysubstituted arylmethyl group of the formula

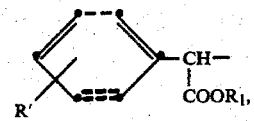

wherein R' is hydrogen, hydroxy, protected hydroxy, acetoxy, $C_1$-$C_3$ alkyl, or halogen;

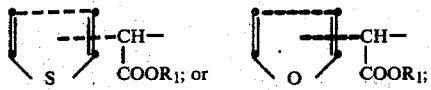

R° is hydrogen or methoxy;
$R_1$ and $R_1'$ are hydrogen or a carboxy protecting group; and when $R_1$ and $R_1'$ are hydrogen, the pharmaceutically acceptable non-toxic salts thereof.

2. The compound of claim 1 wherein R is a group of the formula

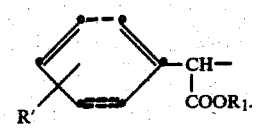

3. The compound of claim 3 wherein R' is hydrogen, hydroxy, or acetoxy.
4. The compound of claim 3 wherein R° is methoxy.
5. The compound of claim 4 wherein R' is hydroxy or protected hydroxy.
6. The compound of claim 5 of the formula

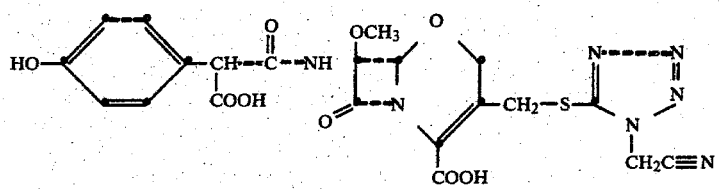

and the pharmaceutically acceptable non-toxic salts thereof.
7. The compound of claim 5 of the formula

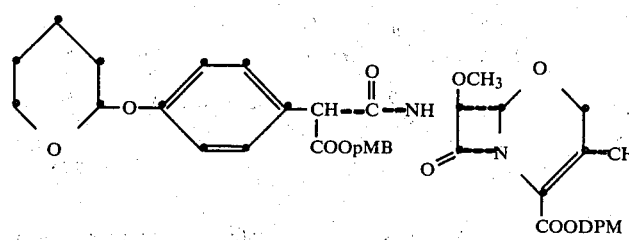 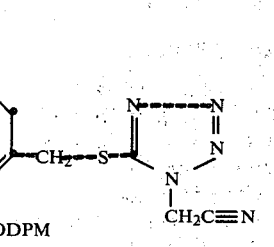
wherein pMB is p-methoxybenzyl and DPM is diphenylmethyl.
8. The compound of claim 5 of the formula
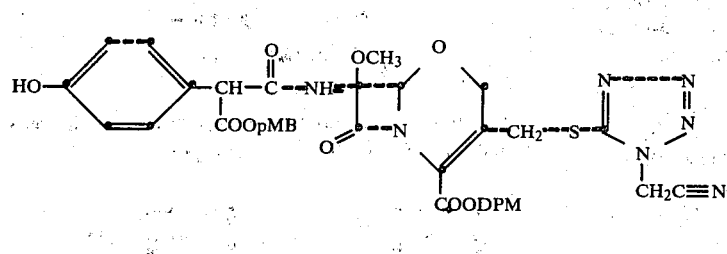
wherein pMB is p-methoxybenzyl and DPM is diphenylmethyl.
9. The compound of claim 1 wherein R is a group of the formula
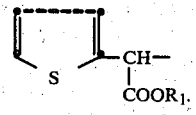
10. The compound of claim 1 wherein R is a group of the formula
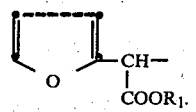
* * * * *